United States Patent [19]
Spahn et al.

[11] Patent Number: 5,328,445
[45] Date of Patent: Jul. 12, 1994

[54] INFLATABLE FOOT CUSHION

[75] Inventors: James G. Spahn, Indianapolis; Steven P. Langley, Martinsville, both of Ind.

[73] Assignee: EHOB, Inc., Indianapolis, Ind.

[21] Appl. No.: 5,901

[22] Filed: Jan. 15, 1993

[51] Int. Cl.⁵ .................................... A61F 5/00
[52] U.S. Cl. ................................ 602/13; 602/23; 128/882
[58] Field of Search ....... 128/845, 882, 892, DIG. 20; 602/5, 6, 12, 13, 23, 28, 29; 607/108, 111

[56] References Cited

U.S. PATENT DOCUMENTS

| | | | |
|---|---|---|---|
| 3,164,152 | 1/1965 | Nicoll | 602/13 |
| 3,351,055 | 11/1967 | Gottfried | |
| 3,786,805 | 1/1974 | Tourin | 602/13 |
| 3,930,496 | 1/1976 | Gibbons | |
| 4,071,031 | 1/1978 | Lowman | |
| 4,197,845 | 4/1980 | Browning | |
| 4,263,905 | 4/1981 | Couch, Jr. | |
| 4,266,298 | 5/1981 | Graziano | 602/13 X |
| 4,399,815 | 8/1983 | Bachorik | 602/13 X |
| 4,624,248 | 11/1986 | Poole et al. | 602/13 |
| 4,730,610 | 3/1988 | Graebe | |
| 4,841,957 | 6/1989 | Wooten et al. | |
| 4,938,208 | 7/1990 | Dye | 602/13 |
| 5,085,214 | 2/1992 | Barrett | |
| 5,125,400 | 6/1992 | Johnson, Jr. | |
| 5,218,954 | 10/1993 | van Bemmelen | 602/13 X |
| 5,226,245 | 7/1993 | Lamont | 128/892 X |

Primary Examiner—Richard J. Apley
Assistant Examiner—Linda C. M. Dvorak
Attorney, Agent, or Firm—Woodard, Emhardt, Naughton, Moriarty & McNett

[57] ABSTRACT

A substantially pillow-shaped, inflatable second cushion that is separable and removably interconnected together with the first cushion maintains proper foot flexion when the body is in the supine position, and is removable to allow ambulation while the foot and lower leg remain cradled in the first cushion. A substantially pillow-shaped, inflatable third cushion is pivotally attached to the bottommost compartments of the first cushion and is pivotally positionable either directly under the Achilles' heel area, or directly under the heel area, or tucked forward of the heel area to provide light compression of the ankle, foot and heel areas. An integral shoe spoon attached to the first cushion prevents the foot cushion from catching bed clothing. A rigid base is provided for rigidly fixing the first inflatable cushion in position to prevent contraction of the feet of comatose patients, for example. A novel connector with two-finger pinch-to-open releasing action provides easily adjustable straps to secure the first cushion non-circumferentially about a foot and lower leg.

12 Claims, 7 Drawing Sheets

INFLATABLE FOOT CUSHION

BACKGROUND OF THE INVENTION

The present invention relates generally to the field of inflatable devices for supporting the human body, and more particularly is concerned with an inflatable foot cushion to counter the force amplifications experienced by the foot, and particularly the heel area of the foot, when the body is in the supine position.

In the supine position, the foot assumes the shape of a wedge that tapers from the toes down to the heel. The force amplifications that are typically associated with a wedge are therefore also experienced by the wedge-shaped foot. The heel area, and more specifically the points of contact between the heel area and the substrate upon which the body is lying in the supine position, experiences force amplifications analogous to those experienced by the working edge of the typical wedge. In addition, when in the supine position, the lower legs function as levers with the heel areas serving as fulcrums, further amplifying the forces acting upon the foot.

These force amplifications associated with the foot, and particularly the heel area of the foot, increase the danger to the soft tissues of the foot and heel areas by, increasing the likelihood of decubitus ulcer formation, for example. Heretofore, devices for preventing the formation of decubitus ulcers on the heel area have not effectively countered these force amplifications experienced by the foot when the body is in the supine position. Merely elevating the foot with a pad, or the like, to suspend the heel area above the substrate upon which the body is lying in the supine position, simply transfers the force amplifications from the heel area to the area of contact between the pad and the ankle or lower leg area. The new area of contact would still be the fulcrum for the lever-like action of the lower leg, and now also the foot. Alternatively, merely wrapping the foot and lower leg areas with padding is equally unsatisfactory if the circumferential contacts of the padding and means for securing the padding to the foot and lower leg areas restrict the blood flow to the lower leg and foot.

SUMMARY OF THE INVENTION

The inflatable foot cushion of the present invention effectively counters the force amplifications experienced by the foot and lower leg when the body is in the supine position, including the force amplifying lever and fulcrum interaction of the lower leg and heel area. A substantially boat-shaped, inflatable first cushion having a plurality of substantially pillow-shaped hydrostatic compartments in fluid communication together cradles the foot and lower leg non-circumferentially and without restricting blood or ambient air flow. A substantially pillow-shaped, inflatable second cushion that is separable and removably interconnected together with the first cushion maintains proper foot flexion when the body is in the supine position, and is removable to allow ambulation while the foot and lower leg remains cradled in the first cushion. A substantially pillow-shaped, inflatable third cushion is pivotally attached to the bottommost compartments of the first cushion and is pivotally positionable either directly under the Achilles' heel area, or directly under the heel area, or tucked forward of the heel area to provide light compression of the ankle, foot and heel areas. An integral shoe spoon attached to the first cushion prevents the foot cushion from catching bed clothing. A rigid base is provided for rigidly fixing the first inflatable cushion in position to prevent contraction of the feet of comatose patients, for example. A novel connector with two-finger pinch-to-open releasing action provides easily adjustable straps to secure the first cushion non-circumferentially about a foot and lower leg.

One embodiment of the present invention is an inflatable foot cushion to reduce the force amplifications upon the foot when the body is in the supine position, comprising: a substantially boat-shaped, inflatable first cushion having a first end, a second end, and including a plurality of substantially pillow-shaped compartments in fluid communication together, and further including a through space between the first end and the bottommost compartments of the first cushion; a substantially pillow-shaped, inflatable second cushion that is separable and removably interconnected together with the first end of the first cushion between the first end and the through space; a substantially pillow-shaped, inflatable third cushion pivotally attached to the bottommost compartments of the first cushion closest to the through space, the third cushion being pivotal between a first position in which the third cushion and the bottommost compartments of the first cushion are positioned together in a vertical stack, and a second position in which the third cushion and the bottommost compartments of the first cushion are positioned together in substantial alignment and in which the third cushion substantially covers the through space, and a third position in which the third cushion is tucked into the through space and is positioned between the second cushion and the bottommost compartments of the first cushion; a valve means on the first, second and third cushions to allow inflation of each to a desired internal pressure; and strap means to adjustably secure the first cushion non-circumferentially about a foot and lower leg with the heel of the foot positioned over the through space.

Another embodiment of the present invention is an inflatable foot cushion to reduce the force amplifications upon the foot when the body is in the supine position, comprising: a substantially boat-shaped, inflatable first cushion having a first end, a second end, and including a plurality of substantially pillow-shaped compartments in fluid communication together, and further including a through space between the first end and the bottommost compartments of the first cushion; a substantially pillow-shaped, inflatable third cushion pivotally attached to the bottommost compartments of the first cushion closest to the through space, the third cushion being pivotal between a first position in which the third cushion and the bottommost compartments of the first cushion are positioned together in a vertical stack, and a second position in which the third cushion and the bottommost compartments of the first cushion are positioned together in substantial alignment and in which the third cushion substantially covers the through space, and a third position in which the third cushion is tucked into the through space and is positioned between the first end of the first cushion and the bottommost compartments of the first cushion; a valve means on the first, second and third cushions to allow inflation of each to a desired internal pressure; and strap means to adjustably secure the first cushion non-circumferentially about a foot and lower leg when the heel of a foot is positioned over the through space.

Yet another embodiment of the present invention is an inflatable foot cushion to reduce the force amplifications upon the foot when the body is in the supine position, comprising: a substantially boat-shaped, inflatable first cushion having a first end, a second end, and including a plurality of substantially pillow-shaped compartments in fluid communication together, and further including a through space between the first end and the bottommost compartments of the first cushion; a substantially pillow-shaped, inflatable second cushion that is separable and removably interconnected together with the first end of the first cushion between the first end and the through space; a substantially pillow-shaped, inflatable third cushion pivotally attached to the bottommost compartments of the first cushion closest to the through space, the third cushion being pivotal between a first position in which the third cushion and the bottommost compartments of the first cushion are positioned together in a vertical stack, and a second position in which the third cushion and the bottommost compartments of the first cushion are positioned together in substantial alignment and in which the third cushion substantially covers the through space, and a third position in which the third cushion is tucked into the through space and is positioned between the second cushion and the bottommost compartments of tile first cushion; a valve means on the first, second and third cushions to allow inflation of each to a desired internal pressure; strap means to adjustably secure the first cushion non-circumferentially about a foot and lower leg with the heel of the foot positioned over the through space; and rigid support means that is separable and removably attached to the first chamber to prevent the contraction of a foot that has been secured within the first chamber.

Yet another embodiment of the present invention is a connector, comprising: a button supported upon a base member; a closure member connected to the base member and having a pair of pinch tabs; and a through hole means disposed between the pinch tabs, the through hole means being sized to snappingly receive the button in locking relationship when the pinch tabs are in substantially planar relationship with the through hole means, and elliptically distorting when the pinch tabs are pinched between a thumb and first finger into a non-planar relationship with the through hole means thereby freeing said closure member from its locking engagement with the button.

It is an object of the present invention to provide a compact, inflatable, hydrostatic foot cushion that effectively decreases the force amplifications upon the foot and heel areas when the body is in the supine position, including the force amplifying lever and fulcrum interaction of the lower leg and heel.

It is a further object of the present invention to provide a compact, inflatable, hydrostatic foot cushion that effectively decreases the force amplifications upon the Achilles' heel area when the body is in the supine position.

It is a further object of the present invention to provide a compact, inflatable, hydrostatic foot cushion that maintains proper foot flexion and prevents foot drop when the body is in the supine position.

It is a further object of the present invention to provide a compact, inflatable, hydrostatic foot cushion that is supportable by a removable rigid base to prevent the contraction of a comatose patient's foot.

It is a further object of the present invention to provide a novel connector with a two-finger pinch-to-open releasing action.

Related objects and advantages of the present invention will be evident from the following descriptions.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, in FIGS. 1a–1e there is illustrated an exploded top plan view of the deflated components of the preferred embodiment of the inflatable foot cushion 10 of the present invention to more clearly illustrate the relationship of these components in the drawing views that follow. Inflatable foot cushion 10 of the preferred embodiment includes three inflatable cushions, a first cushion 12, a second cushion 14 and a third cushion 16. Each of these cushions 12, 14, and 16 have been formed from a pair of pliable plastic sheets that have been peripherally joined together by conventional means to form a pressurizable chamber. As illustrated in FIG. 1, in the preferred embodiment, cushions 12 and 16 have been constructed from the same pair of plastic sheets. Cushions 12 and 16 share a common peripheral boundary 24 where the pair of plastic sheets have been fused together by conventional means. Peripheral boundary 24 terminates at each of its ends with through holes 28, formed by cutting out circular portions of the pair of plastic sheets and joining the pair of plastic sheets together about the circumference of the through holes 28. Along peripheral edges 26 of cushion 12, the peripheral edges of the pair of plastic sheets forming cushion 12 are joined together, again by conventional means, as are the peripheral edges 27 of the pair of plastic sheets directly opposite peripheral edges 26 that form cushion 16. The common joinder of the pair of plastic sheets forming cushions 12 and 16 along edges 26 of cushion 12 and edges 27 of cushion 16 are then cut along the edges 26 and 27 from through holes 28 to the first end 30 of first cushion 12, thus separating cushion 12 from cushion 16 by separating edges 26 and 27 of cushions 12 and 16, respectively.

Cushion 12 is further divided into a plurality of substantially pillow-shaped compartments 32, 34, 36, 38, 40, and 42 by selectively providing additional through holes 44 in the same manner as through holes 28 were provided, and by fusing the pair of plastic sheets forming cushion 12 together along lines 46 and 48 from through holes 44 to the second end 50 of cushion ]2. In addition, through hole 52 is provided in cushion 12 in the same manner as through holes 44, and the pair of plastic sheets forming cushion 12 are fused together along band 54, which is about the width of the diameter of through hole 52 and runs from through hole 52 to the second end 50 of cushion 12.

Also located at the second end 50 of cushion 12 is a spoon flap 51 formed in the same manner as cushions 12 and 16. Spoon flap 51 is disposed at the second end of cushion 12 to prevent the second end of cushion 12 from becoming caught upon bed clothing when cushion 12 is secured about the foot and lower leg area in the manner described below to a person reclining in the supine position on a substrate surface covered with typical bed clothing.

About the periphery of cushion 12 there are provided a plurality of slits 56 cut through the joined pair of plastic sheets forming cushion 12 that are sized to receive straps 58 and 60, which are the preferred strap means of the preferred embodiment to adjustably secure inflated cushion 12 about a foot and lower leg, as will be described further, below. Similarly, band 54 has been provided with slits 56, as well, for the same purpose. Cushion 16 has also been provided with a tab 63 formed by joining the pair of plastic sheets that form cushion 16, which has also been provided with slits 62 formed in the same manner as slits 56, but sized to receive tabs 64 and 66 of cushion 14, as will be described, below. Cushion 12 has also been provided with slits 62 in its peripheral edges at its first end 30, also sized to receive tabs 64 and 66 of cushion 14, as will be described, below.

Figure 11:
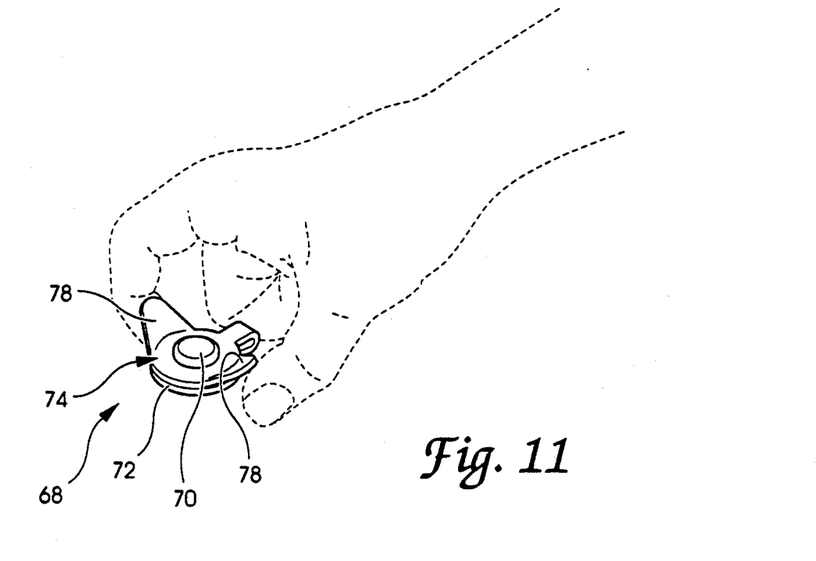
FIG. 11 is a perspective view of the connector means of FIG. 7 in the pinch-to-open configuration, with an operator's hand shown in dotted outline.

A novel connector 68 (see also FIGS. 7-10) has a button 70 that is snugly received by through holes 59 and 61 in straps 58 and 60, and by through holes 65 and 67 in tabs 64 and 66 of cushion 14. Button 70 is supported upon a base member 72, which is connected to a closure member 74 having a pair of pinch tabs 78 and a through hole 76 therebetween. Through hole 76 is sized to snugly receive button 70. Connector 68 is constructed from a relatively pliable plastic material such that the through hole 76 may be sized to cause closure member 74 to snap onto button 70 when pinch tabs 78 are substantially planar with through hole 76, but such that through hole 76 elliptically distorts when pinch tabs 78 are pinched between a thumb and first finger, for example (see FIG. 11) thereby allowing closure member 74 to be freed from its engagement with button 70. Connector 68 is the preferred connector for all removable connections of the preferred embodiment as it resists unsnapping under shear stresses, yet is easily released by pinching tabs 78 with two fingers of one hand.

In the preferred embodiment to date, cushions 12, 14, and 16 have been provided with conventional air valves 18, 22, and 20, respectively (see also FIGS. 2, 4, and 5), to permit the pressurization and resulting inflation of each of the cushions 12, 14, and 16 with air. Alternatively, suitable valving could be provided to permit the pressurization and resulting inflation of each of the cushions 12, 14, and 16 with other gases, or with liquids, or semi-solids.

Figure 1A:
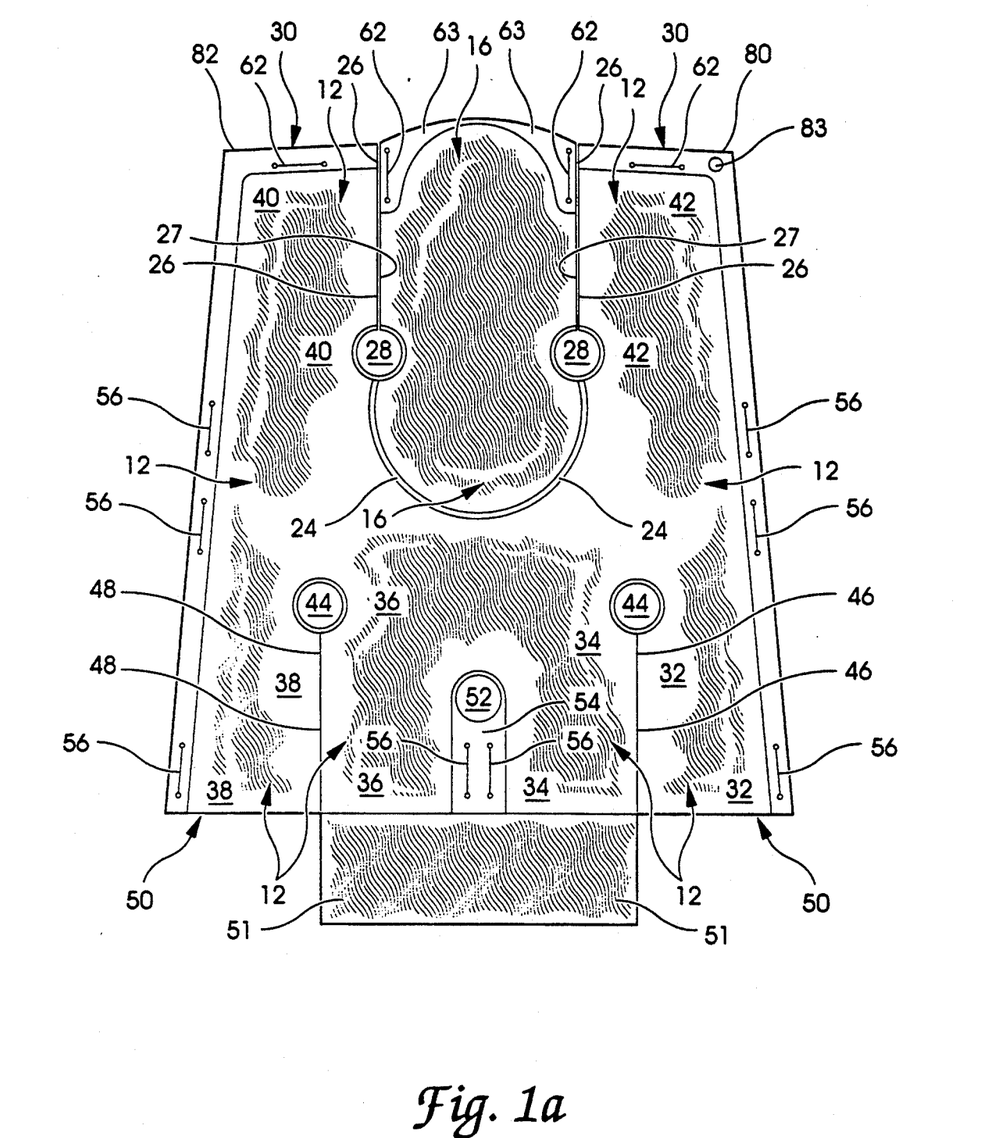
FIGS. 1a–1e is an exploded top plan view of the deflated first, second and third cushions, the preferred strap means, and the preferred connector means of the preferred embodiment of the inflatable foot cushion of the present invention to more clearly illustrate the relationship of these components of the present invention.
Figure 1B:
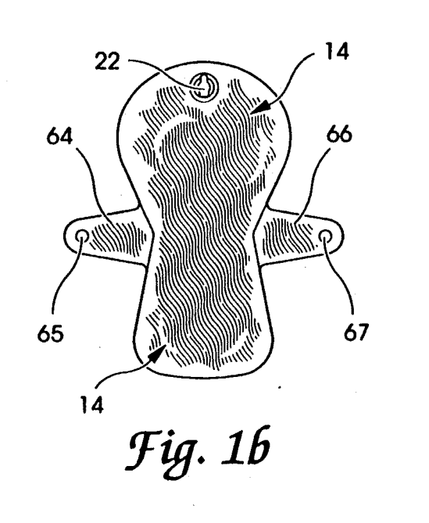
Figure 1C:
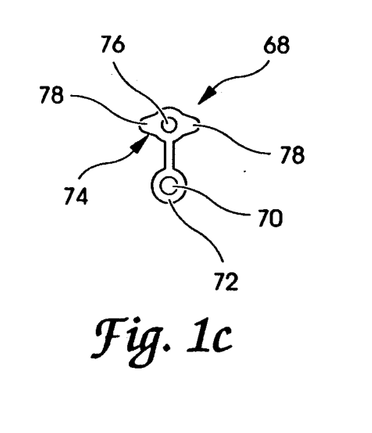
Figure 1D:
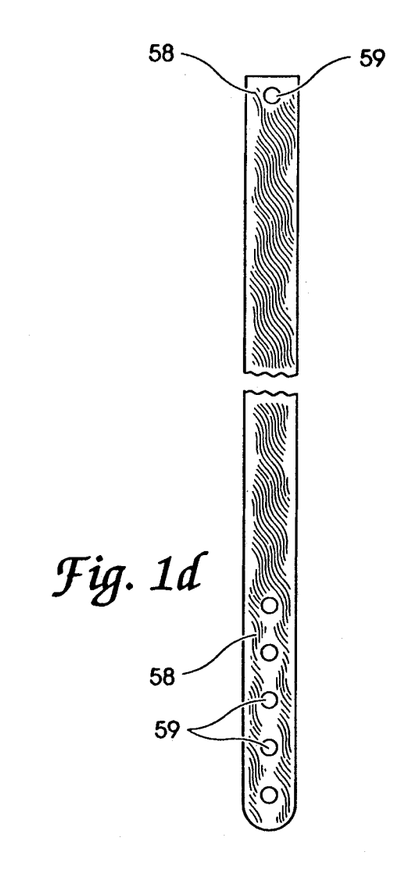
Figure 1E:
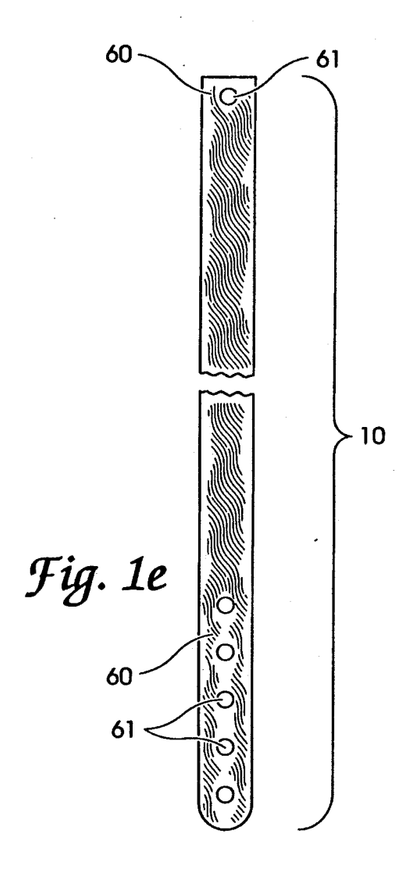
Figure 2:
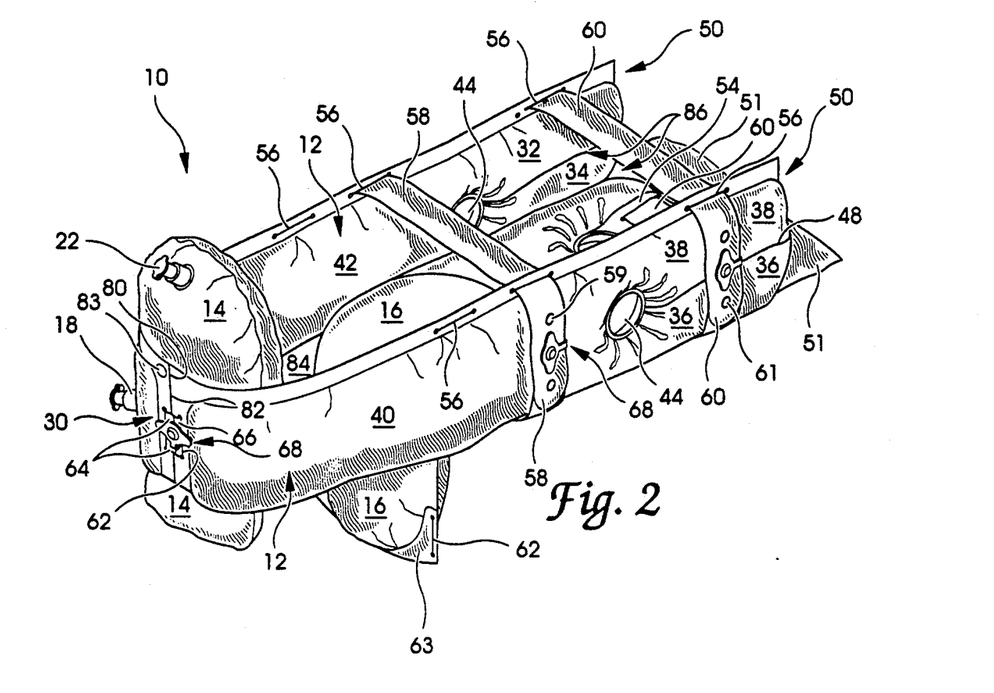
FIG. 2 is a perspective view of the inflatable foot cushion of FIGS. 1a–1e assembled and with the first, second and third inflatable cushions inflated.
Figure 3:
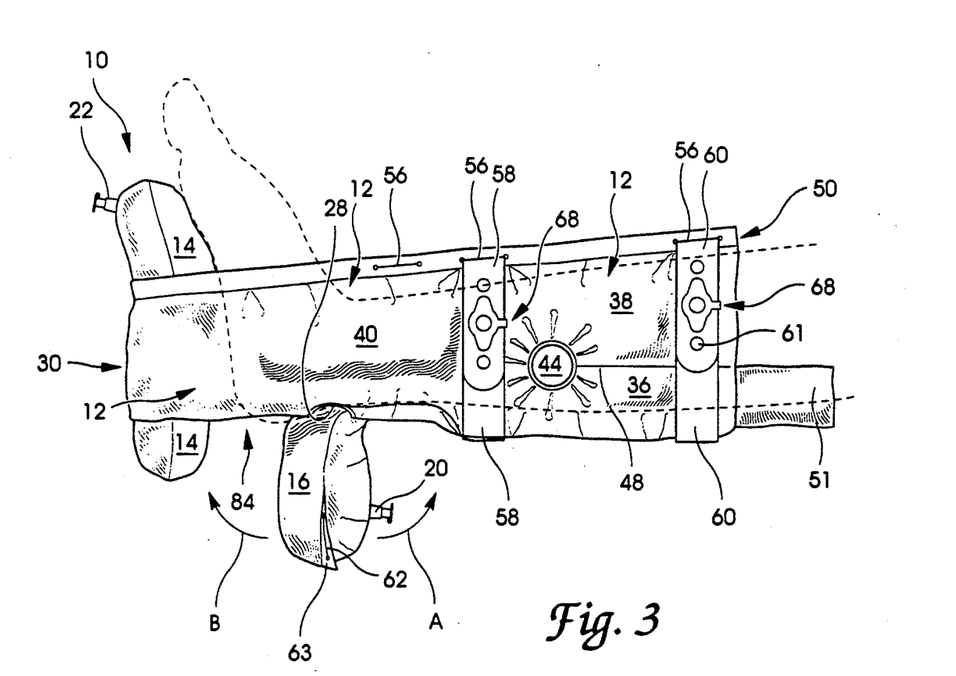
FIG. 3 is a right side elevation view of the inflatable foot cushion of FIG. 2 with a lower leg and foot in the supine position shown in dotted outline.
Figure 4:
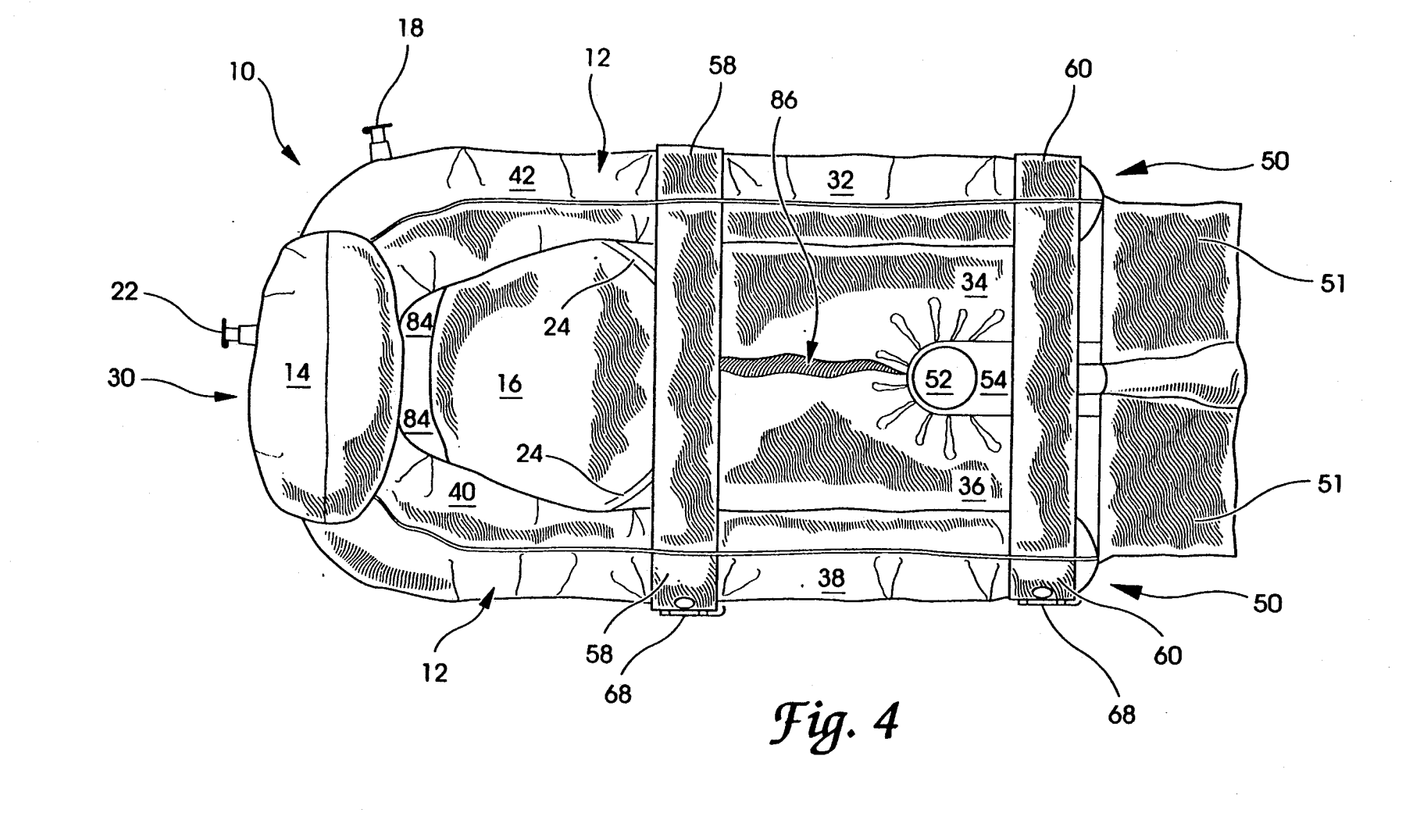
FIG. 4 is a top plan view of the inflatable foot cushion of FIG. 2.
Figure 5:
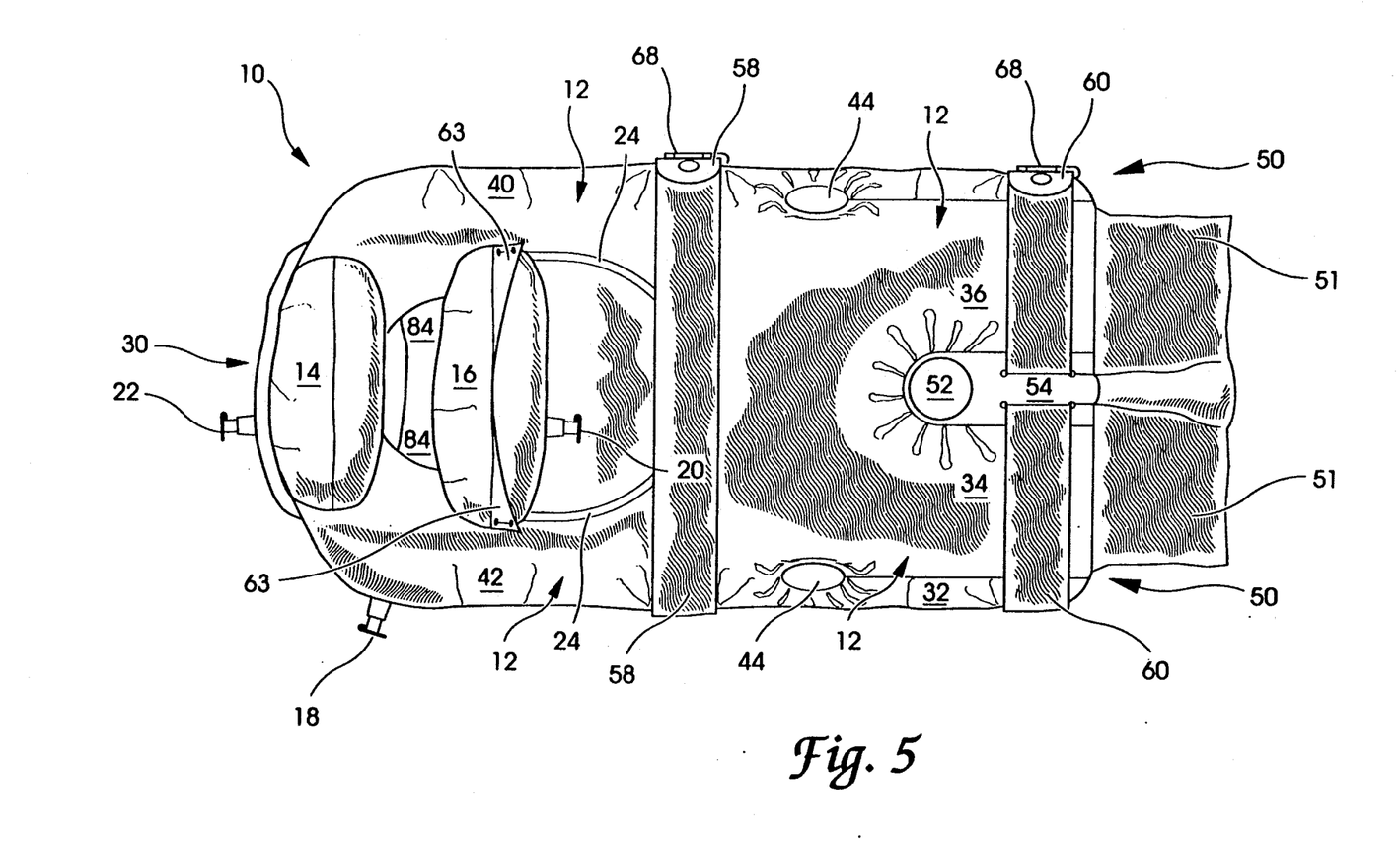
FIG. 5 is a bottom plan view of the inflatable foot cushion of FIG. 2.

Referring now to FIGS. 2-5, cushion 12 assumes the substantially boat-shaped configuration with an essentially wedge-shaped bow as illustrated in these drawings by overlapping peripheral edges 80 and 82 of the first end 30 of cushion 12 (FIGS. 1a-1e), fusing the four layers of plastic material together, and then pressurizing the inflatable cushions 12, 14, and 16 to inflate them with air to desired levels. Reference is made to circle labeled 83 for proper orientation between FIGS. 1a-1e and FIGS. 2-5. As illustrated in FIGS. 2 and 4, compartments 34 and 36 are the bottommost compartments of cushion 12, and compartments 32, 38, 40 and 42 become the sides of the substantially boat-shaped cushion 12, which are held in this relative position by straps 58 and 60 as illustrated in FIGS. 2-5. As clearly illustrated in FIG. 3, cushion 16, without being under any other influence, drops downwardly and freely pivots in the direction of the arrows in FIG. 3 about an axis that lies approximately between the center points of through holes 28 (FIGS. 1a-1e). When disposed in the position illustrated in FIG. 3, a through space 84 through cushion 12 is created between the first end and the bottommost compartments 34 and 46 of cushion 12.

Continuing to refer to FIGS. 2-5, substantially pillow-shaped cushion 14 is removably interconnected together with the first end 30 of cushion 12 between the first end 30 and the through space 84 by lacing tabs 64 and 66 of cushion 14 through slits 62 at the first end 30 of cushion 12, aligning the through holes 65 and 67 of tabs 64 and 66, and attaching a connector 68 through the aligned through holes 65 and 67 (FIG. 2).

Referring now to FIG. 3, there is illustrated in outline form the position a foot and lower leg would assume when the inflatable cushion of the present invention is non-circumferentially secured about the foot and lower leg, with the heel area positioned over the through space 84. Straps 58 and 60, in cooperation with connectors 68, adjustably secure the straps in place above the leg so as to avoid blood flow restrictions. The leg and foot are hydrostatically cushioned and cradled in a non-compromising fashion within cushion 12 by the pillow shaped compartments 32, 34, 36, 38, 40, and 42 of cushion 12. MRT and CAT scans have demonstrated in testing completed to date that there is no compromising of the blood flow or soft tissue structure in the lower leg and foot areas by cushion 12, and through holes 28, 44, and 52, in cooperation with the troughs 86 defined in the inflated cushion 12 by their corresponding peripheral joints and lines, i.e., 24, 48, 54, and 46, provide ambient air circulation around the foot and leg. Cushion 14 comfortably holds the foot at about the desirable 30 degrees of foot flexion.

Continuing to refer to FIG. 3, as can be seen from the illustration, cushion 16 is pivotal into a number of different positions, including the following. Cushion 16 is pivotal in the direction of arrow A into a first position at which cushion 16 and the bottommost compartments 34 and 36 of cushion 12 are positioned together in a vertical stack. Cushion 16 could be secured in place by lacing the strap 58 through slits 62 provided on tab 63 of cushion 16. In this described first position, the heel area would be elevated and would be free from any contact with cushion 16 or any substrate surface, as cushion 12 would rest only upon cushion 16. Cushion 16 is also pivotal in the direction of arrow B into a second position in which cushion 16 and the bottommost compartments 34 and 36 of cushion 12 are positioned together in substantial planar alignment (such as in FIGS. 1a–1e) and in which cushion 16 substantially covers the through space 84. In this described second position, the heel area would be resting upon cushion 16 and the Achilles tendon would be free from direct contact with cushion 16 or any substrate surface. Cushion 16 may also be pivoted farther in the direction of arrow B and farther than the second position described, above, by tucking tab 63 into the through space 84 between cushion 14 and bottommost compartments 34 and 36 of cushion 12. In this described third position, the heel would be resting upon a tucked up cushion 16 and the heel and ankle areas of the foot would experience a light compression by reason of this described third position of cushion 16.

Figure 6:
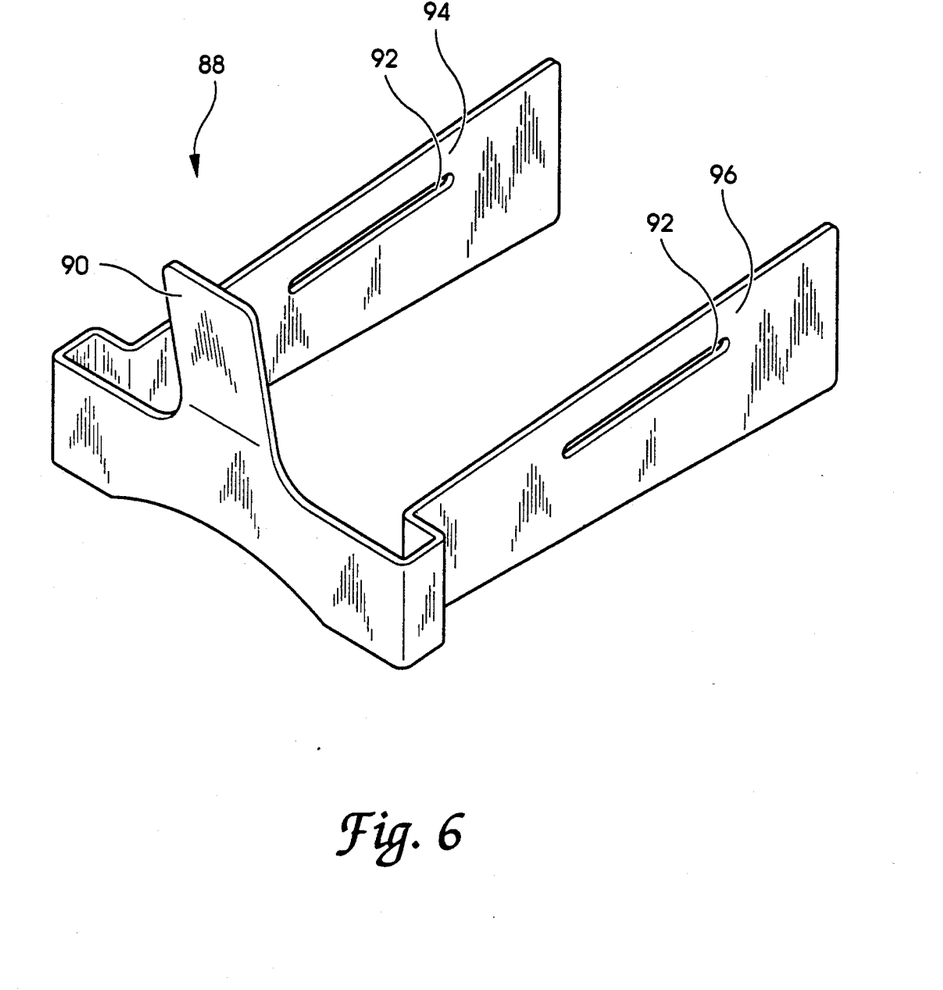
FIG. 6 is a perspective view of the preferred embodiment of the rigid support means of the present invention.
Figure 7:
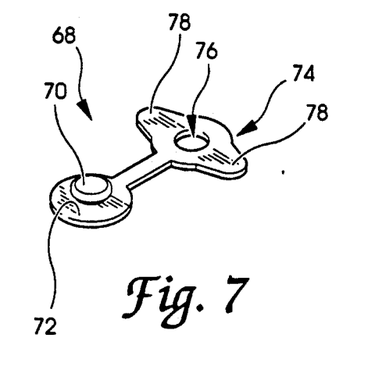
FIG. 7 is a perspective view of the preferred connector means of the present invention.
Figure 8:
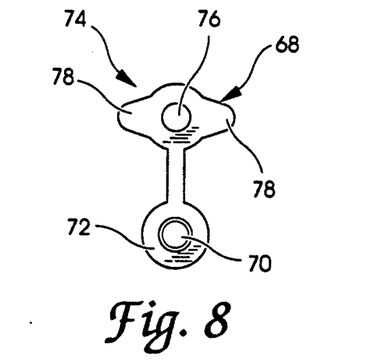
FIG. 8 is top plan view of the connector means of FIG. 7.
Figure 9:
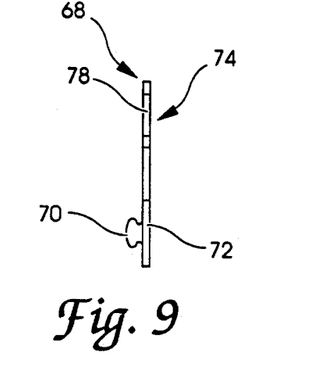
FIG. 9 is a right side elevation view of the connector means of FIG. 7.
Figure 10:
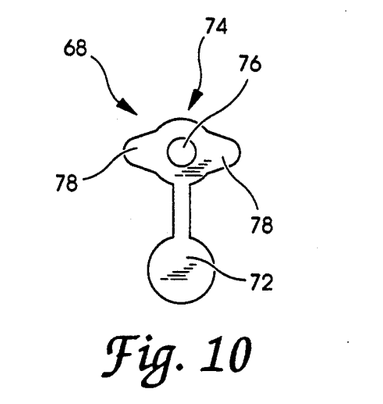
FIG. 10 is a bottom plan view of the connector means of FIG. 7.

Referring now to FIG. 6, there is illustrated the preferred rigid support means for the inflatable foot cushion 10 of the present invention. Rigid support 88 has a tongue 90 that is insertable between cushion 14 and its tabs 64 and 66 when in their respective positions illustrated in FIG. 2. In this position, the arms 94 and 96 would parallel compartments 42 and 32, and 40 and 48, respectively, of cushion 12. Through slots 92 are provided in arms 94 and 96 to accommodate the securing attachment of straps 58 an 60. Rigid support 88 is thus attachable to first cushion 12 to prevent the contraction of a foot that has been secured within cushion 12.

From the foregoing descriptions, it will be appreciated by those skilled in the medical arts that the novel inflatable foot cushion 10 of the present invention effectively de-wedges the wedge-shaped foot by cradling the foot in the essentially wedge-shaped bow of the substantially boat-shaped cushion 12, thus reducing the associated force amplifications experienced by the lower leg and foot areas when they are in the supine position. Cushion 16 provides a substantially pillow-shaped cushion that may be separably inflated to the desired internal pressure and positioned in a way that will effectively accommodate varying needs in the heel and Achilles' tendon complex. Removable cushion 14 allows a wearer of the inflatable foot cushion 10 to ambulate by removing cushion 14 from its engagement with cushion 12.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An inflatable foot cushion to reduce the force amplifications upon the foot when the body is in the supine position, comprising:
    a substantially boat-shaped, inflatable first cushion having a first end, a second end, and including a plurality of substantially pillow-shaped compartments in fluid communication together that define the sides and bottom of said first cushion, and further including a through space between the first end and the bottom compartments of said first cushion;
    a substantially pillow-shaped, inflatable second cushion that is separable and removably interconnected together with the first end of said first cushion between said first end and said through space;
    a substantially pillow-shaped, inflatable third cushion pivotally attached to the bottom compartments of said first cushion closest to said through space, said third cushion being pivotal between a first position in which said third cushion and the bottom compartments of said first cushion are positioned together in a vertical stack, and a second position in which said third cushion and the bottom compartments of said first cushion are positioned together in substantially planar alignment and in which said third cushion substantially covers said through space, and a third position in which said third cushion is tucked into said through space and is positioned between said second cushion and the bottom compartments of said first cushion;
    a valve means on said first, second and third cushions to allow inflation of each to a desired internal pressure; and
    strap means to adjustably secure said first cushion non-circumferentially about a foot and lower leg when the heel of a foot is positioned over said through space.

2. The inflatable foot cushion of claim 1 wherein the substantially pillow-shaped compartments of said first cushion are sized and arranged in an order so that adjacent inflated compartments define external troughs between them over which ambient air may circulate.

3. The inflatable foot cushion of claim 2 wherein a plurality of said external troughs are further provided with through holes in said first cushion through which ambient air may circulate.

4. The inflatable foot cushion of claim 1, and further comprising spoon flap means disposed at the second end of said first cushion to prevent the second end of said first cushion from becoming caught upon bed clothing.

5. An inflatable foot cushion to reduce the force amplifications upon the foot when the body is in the supine position, comprising;
    a substantially boat-shaped, inflatable first cushion having a first end, a second end, and including a plurality of substantially pillow-shaped compartments in fluid communication together that define the sides and bottom of said first cushion, and further including a through space between the first end and the bottom compartments of said first cushion;
    a substantially pillow-shaped, inflatable third cushion pivotally attached to the bottom compartments of said first cushion closest to said through space, said third cushion being pivotal between a first position in which said third cushion and the bottom compartments of said first cushion are positioned together in a vertical stack, and a second position in which said third cushion and the bottom compartments of said first cushion are positioned together in substantially planar alignment and in which said third cushion substantially covers said through space, and a third position in which said third cushion is tucked into said through space and is positioned between the first end of said first cushion and the bottom compartments of said first cushion;

a valve means on said first and third cushions to allow inflation of each to a desired internal pressure; and strap means to adjustably secure said flat cushion non-circumferentially about a foot and lower leg when the heel of a foot is positioned over said through space.

6. The inflatable foot cushion of claim 5 wherein the substantially pillow-shaped compartments of said first cushion are sized and arranged in an order so that adjacent inflated compartments define external troughs between them through which ambient air may circulate.

7. The inflatable foot cushion of claim 6 wherein a plurality of said external troughs are further provided with through holes in said first cushion through which ambient air may circulate.

8. The inflatable foot cushion of claim 5, and further comprising spoon flap means disposed at the second end of said first cushion to prevent the second end of said first cushion from becoming caught upon bed clothing.

9. An inflatable foot cushion to reduce the force amplifications upon the foot when the body is in the supine position, comprising:

a substantially boat-shaped, inflatable first cushion having a first end, a second end, and including a plurality of substantially pillow-shaped compartment sin fluid communication together that define the sides and bottom of said first cushion, and further including a through space between the first end and the bottom compartments of said first cushion;

a substantially pillow-shaped, inflatable second cushion that is separable and removably interconnected together with the first end of said first cushion between said first end and said through space;

a substantially pillow-shaped, inflatable third cushion pivotally attached to the bottom compartments of said first cushion closest to said through space, said third cushion being pivotal between a first position in which said third cushion and the bottommost compartments of said first cushion are positioned together in a vertical stack, and a second position in which said third cushion and the bottom compartments of said first cushion are positioned together in substantially planar alignment and in which said third cushion substantially covers said through space, and a third position in which said third cushion is tucked into said through space and is positioned between said second cushion and the bottom compartments of said first cushion;

a valve means on said first, second and third cushions to allow inflation of each to a desired internal pressure;

strap means to adjustably secure said first cushion non-circumferentially about a foot and lower leg with the heel of the foot positioned over said through space; and rigid support means that is separable and removably attached to said first cushion to prevent the contraction of a foot that has been secured within said first cushion.

10. The inflatable foot cushion of claim 9 wherein the substantially pillow-shaped compartments of said first cushion are sized and arranged in an order so that adjacent inflated compartments define external troughs between them over which ambient air may circulate.

11. The inflatable foot cushion of claim 10 wherein a plurality of said external troughs are further provided with through holes in said first cushion through which ambient air may circulate.

12. The inflatable foot cushion of claim 9, and further comprising spoon flap means disposed at the second end of said first cushion to prevent the second end of said first cushion from becoming caught upon bed clothing.

* * * * *

UNITED STATES PATENT AND TRADEMARK OFFICE
CERTIFICATE OF CORRECTION

PATENT NO. : 5,328,445
DATED : July 12, 1994
INVENTOR(S) : James G. Spahn, et al It is certified that error appears in the above-indentified patent and that said Letters Patent is hereby corrected as shown below:

In Col. 3, at line 26, delete "tile" and substitute --the--.

In Col. 5, at line 23, delete "]2" and substitute --12--.

In Col. 9, at line 11, delete "flat" and substitute --first--.

In Col. 9, at line 34, delete "ment sin" and substitute --ments in--.

In Col. 10, at line 7, delete "bottommost" and substitute --bottom--.

Signed and Sealed this

Eighth Day of November, 1994

Attest:

BRUCE LEHMAN

*Attesting Officer*    *Commissioner of Patents and Trademarks*